United States Patent
Garcia Molina et al.

(10) Patent No.: US 11,357,950 B2
(45) Date of Patent: Jun. 14, 2022

(54) SYSTEM AND METHOD FOR DELIVERING SENSORY STIMULATION DURING SLEEP BASED ON DEMOGRAPHIC INFORMATION

(71) Applicants: KONINKLIJKE PHILIPS N.V., Eindhoven (NL); Wisconsin Alumni Research Foundation, Madison, WI (US)

(72) Inventors: Gary Nelson Garcia Molina, Madison, WI (US); Tsvetomira Kirova Tsoneva, Eindhoven (NL); Brady Alexander Riedner, Middleton, WI (US); Giulio Tononi, Verona, WI (US)

(73) Assignees: KONINKLIJKE PHILIPS N.V., Eindhoven (NL); WISCONSIN ALUMNI RESEARCH FOUNDATION, Madison, WI (US)

( * ) Notice: Subject to any disclaimer, the term of this patent is extended or adjusted under 35 U.S.C. 154(b) by 339 days.

(21) Appl. No.: 16/580,845

(22) Filed: Sep. 24, 2019

(65) Prior Publication Data
US 2020/0101262 A1 Apr. 2, 2020

Related U.S. Application Data

(60) Provisional application No. 62/738,246, filed on Sep. 28, 2018.

(51) Int. Cl.
*A61M 21/02* (2006.01)
*A61M 21/00* (2006.01)
*G16H 20/30* (2018.01)

(52) U.S. Cl.
CPC .......... *A61M 21/02* (2013.01); *G16H 20/30* (2018.01); *A61M 2021/0027* (2013.01);
(Continued)

(58) Field of Classification Search
CPC ........ A61M 21/00–02; A61M 2203/10; A61B 5/4806–4815
See application file for complete search history.

(56) References Cited

U.S. PATENT DOCUMENTS 10,137,276 B2 11/2018 Garcia Molina et al.
10,183,142 B2 1/2019 Garcia Molina et al.
(Continued)

FOREIGN PATENT DOCUMENTS

KR 2017028089 A 3/2017

OTHER PUBLICATIONS

Nguyen et al., "Age and Gender Classification Using EEG Paralinguistic Features," 6th Annual International IEEE Embs Conference on Neural Engineering, Nov. 2013 (Year: 2013).*

(Continued)

*Primary Examiner* — Thaddeus B Cox

(57) ABSTRACT

The present disclosure pertains to delivering sensory stimulation to a user during a sleep session. In some embodiments, sensors are configured to generate output signals conveying information related to brain activity of the user during the sleep session. Sensory stimulators are configured to provide the sensory stimulation to the user during the sleep session. One or more processors are configured to determine a demographic group for the user; select a stimulation parameter model associated with the demographic group of the user from a set of stimulation parameter models associated with different demographic groups; and control the one or more sensory stimulators to deliver the sensory stimulation to the user based on the stimulation parameter model for the demographic group of the user and the output signals.

12 Claims, 7 Drawing Sheets

(52) U.S. Cl.
CPC . *A61M 2205/3303* (2013.01); *A61M 2230/10* (2013.01); *A61M 2230/18* (2013.01)

(56) References Cited

U.S. PATENT DOCUMENTS

| | | |
|---|---|---|
| 10,220,183 B2 | 3/2019 | Garcia Molina et al. |
| 2016/0082222 A1 | 3/2016 | Garcia Molina et al. |
| 2016/0296164 A1 | 10/2016 | Garcia Molina et al. |
| 2016/0302718 A1 | 10/2016 | Laura Lapoint et al. |

OTHER PUBLICATIONS

Van Putten et al., "Predicting sex from brain rhythms with deep learning," Sci. Rep. 8, 3069 (Feb. 2018) (Year: 2018).*

Al Zoubi et al., "Predicting Age from Brain EEG Signals—A Machine Learning Approach," Front. Aging Neurosci. 10, 184 (Jul. 2018) (Year: 2018).*

Anonymous, "Delta wave", Aug. 2018.

M. M. Ohayon, M. a Carskadon, C. Guilleminault, and M. V Vitiello, "Meta-analysis of quantitative sleep parameters from childhood to old age in healthy individuals: developing normative sleep values across the human lifespan," Sleep, vol. 27, No. 7, pp. 1255-1273, 2004.

J. Carrier, S. Land, D. J. Buysse, D. J. Kupfer, and T. H. Monk, "The effects of age and gender on sleep EEG power spectral density in the middle years of life (ages 20-60 years old).," Psychophysiology, vol. 38, No. 2, pp. 232-242, 2001.

K. E. Sprecher, B. Riedner, R. F. Smith, G. Tononi, R. J. Davidson, and R. M. Benca, "High resolution topography of age-related changes in non-rapid eye movement sleep electroencephalography," PLoS One, vol. 11, No. 2, pp. 1-16, 2016.

B. A. Mander, J. R. Winer, and M. P. Walker, "Review Sleep and Human Aging," Neuron, vol. 94, No. 1, pp. 19-36, 2017.

E. B. Kierman, W. Wang, J. F. Duffy, D.-J. Dijk, C. a Czeisler, and R. E. Kronauer, "Survival analysis indicates that age-related decline in sleep continuity occurs exclusively during NREM sleep.," Neurobiol. Aging, vol. 34, No. 1, pp. 309-318, Jan. 2013.

* cited by examiner

SYSTEM AND METHOD FOR DELIVERING SENSORY STIMULATION DURING SLEEP BASED ON DEMOGRAPHIC INFORMATION

CROSS-REFERENCE TO PRIOR APPLICATIONS

This application claims the benefit of U.S. Provisional Application No. 62/738,246, filed on 28 Sep. 2018. This application is hereby incorporated by reference herein.

BACKGROUND

1. Field

The present disclosure pertains to a system and method for delivering sensory stimulation during sleep based on demographic information.

2. Description of the Related Art

Systems for monitoring sleep and delivering sensory stimulation to users during sleep are known. Electroencephalogram (EEG) sensor based sleep monitoring and sensory stimulation systems are known. These systems do not account for changes in user characteristics, such as age and other demographic parameters. As a result, users may receive less stimulation than they might otherwise, or the stimulation timing may not adequately correspond to their individual sleeping patterns. Thus, there is a need for a system that is able to adjust stimulation for a sleeping subject depending on their demographic characteristics (e.g., even when an explicit demographic group designation is not yet available for a user).

SUMMARY

Accordingly, one or more aspects of the present disclosure relate to a system configured to deliver sensory stimulation to a user during a sleep session. The system comprises one or more sensors, one or more sensory stimulators, one or more processors, and/or other components. The one or more sensors are configured to generate output signals conveying information related to brain activity of the user during the sleep session. The one or more sensory stimulators are configured to provide the sensory stimulation to the user during the sleep session. The one or more processors are coupled to the one or more sensors and the one or more sensory stimulators. The one or more processors are configured by machine-readable instructions. The one or more processors are configured to determine a demographic group for the user based on the output signals generated during a first sleep session (or portion thereof). The one or more processors are configured to select, during the sleep session, a stimulation parameter model associated with the demographic group of the user from a set of stimulation parameter models associated with different demographic groups. The one or more processors are configured to control, during a second sleep session (or portion thereof), the one or more sensory stimulators to deliver the sensory stimulation to the user based on the stimulation parameter model for the demographic group of the user and the output signals generated during the second portion of the sleep session. The second sleep session is subsequent in time to the first sleep session. In some embodiments, the one or more processors are configured to use the output signals generated during the first sleep session to determine the demographic group for the user based on a lack of an explicit demographic group designation for the user.

Another aspect of the present disclosure relates to a method for delivering sensory stimulation to a user during a sleep session with a delivery system. The system comprises one or more sensors, one or more sensory stimulators, one or more processors, and/or other components. The method comprises generating, with the one or more sensors, output signals conveying information related to brain activity of the user during the sleep session. The method comprises providing, with the one or more sensory stimulators, the sensory stimulation to the user during the sleep session. The method comprises determining, with the one or more processors, a demographic group for the user based on the output signals generated during a first sleep session. The method comprises selecting, with the one or more processors, during the sleep session, a stimulation parameter model associated with the demographic group of the user from a set of stimulation parameter models associated with different demographic groups. The method comprises controlling, with the one or more processors, during a second sleep session, the one or more sensory stimulators to deliver the sensory stimulation to the user based on the stimulation parameter model for the demographic group of the user and the output signals generated during the second portion of the sleep session. The second portion of the sleep session is subsequent in time to the first portion of the sleep session. In some embodiments, the method comprises using the output signals generated during the first portion of the sleep session to determine the demographic group for the user based on a lack of an explicit demographic group designation for the user.

Yet another aspect of the present disclosure relates to a system for delivering sensory stimulation to a user during a sleep session. The system comprises means for generating output signals conveying information related to brain activity of the user during the sleep session. The system comprises means for providing the sensory stimulation to the user during the sleep session. The system comprise means for determining a demographic group for the user based on the output signals generated during a first portion of the sleep session. The system comprises means for selecting, during the sleep session, a stimulation parameter model associated with the demographic group of the user from a set of stimulation parameter models associated with different demographic groups. The system comprises means for controlling, during a second portion of the sleep session, the means for providing the sensory stimulation to deliver the sensory stimulation to the user based on the stimulation parameter model for the demographic group of the user and the output signals generated during the second portion of the sleep session. The second portion of the sleep session is subsequent in time to the first portion of the sleep session. In some embodiments, the output signals generated during the first portion of the sleep session are used to determine the demographic group for the user based on a lack of an explicit demographic group designation for the user.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the

DETAILED DESCRIPTION OF EXEMPLARY EMBODIMENTS

Figure 1:
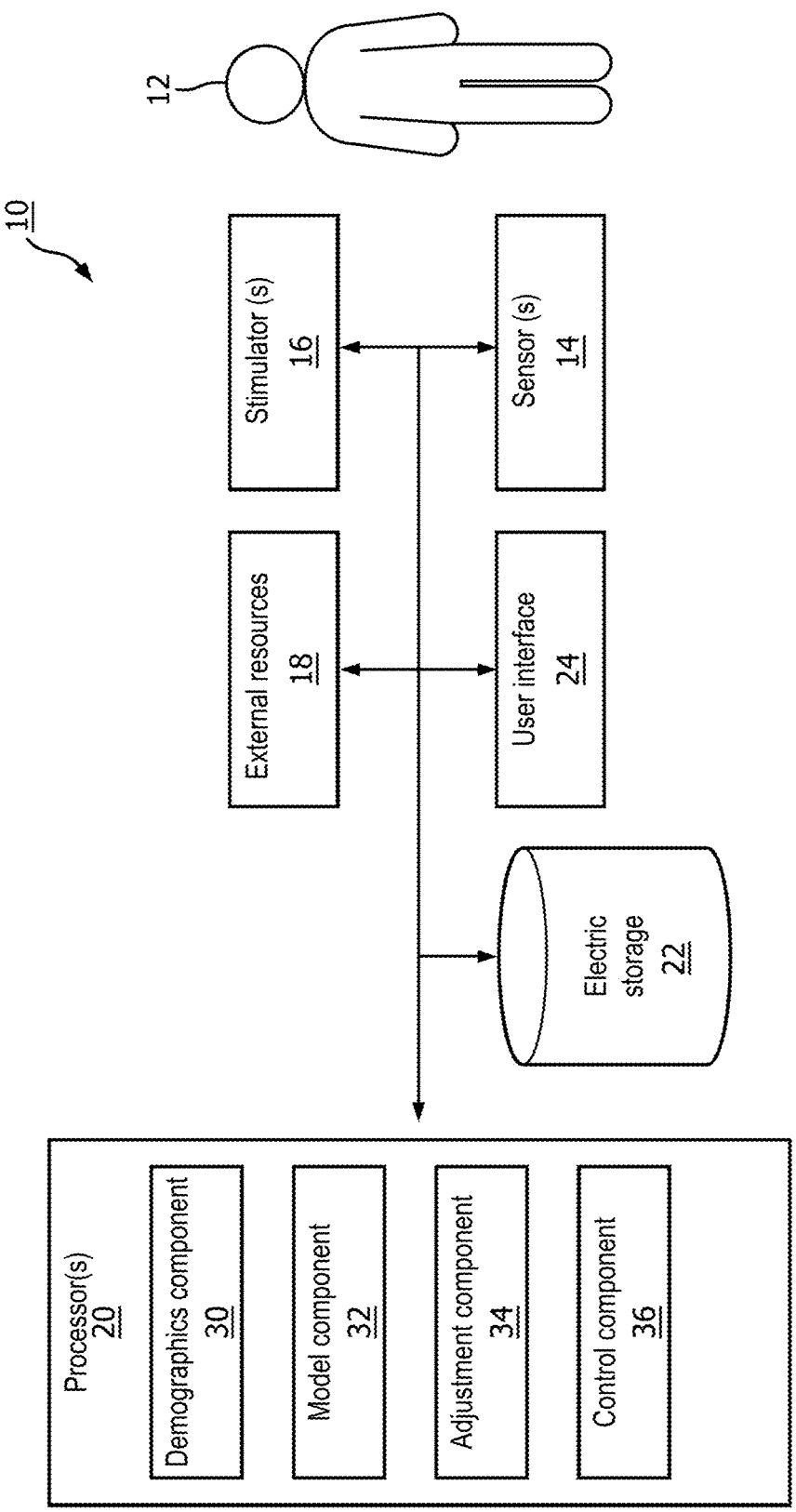
FIG. 1 is a schematic illustration of a system configured to deliver sensory stimulation to a user during a sleep session, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to deliver sensory stimulation to a user 12 during a sleep session. Changes in sleep architecture, spectral properties of the sleep electroencephalogram (EEG), slow wave activity, and NREM (non-rapid eye movement) sleep fragmentation can be attributed to demographic characteristics such as age and gender. These changes may be substantial. System 10 is configured to account for these changes when automatically analyzing sleep data and/or delivering sensory (e.g., auditory) stimulation to enhance slow wave sleep (e.g., as described below). The accumulation of the slow wave activity (cumulative SWA or CSWA) throughout NREM sleep relates to the restorative value of sleep.

As a brief summary (more details are provided below), deep NREM sleep may be detected and sensory (e.g., auditory) stimulation may be delivered to enhance slow wave activity (SWA, i.e. the EEG power in the 0.5 to 4 Hz band). An EEG signal may be filtered in three frequency bands: alpha (8-12 Hz), beta (15-30 Hz), and delta (0.5 to 40 Hz) to obtain root mean square (RMS) power values in each of these bands. Detection of sleep micro-arousals and "wake" states is accomplished by detecting periods for which alpha or beta RMS values exceed predefined thresholds. If the alpha or beta RMS exceed the thresholds for a period lasting at least ten (for example) seconds, a "wake" state may be detected; otherwise a sleep micro-arousal is detected. The presence of a micro-arousal delays the onset of the next auditory stimulation or stops stimulation in case of ongoing stimulation. Deep sleep (e.g., N3 sleep described below) is detected responsive to delta RMS exceeding a predefined threshold for at least some threshold amount of time (e.g., 25 seconds) and responsive to if the number of detected slow waves in a threshold length (e.g., 20-second-long) sliding window is higher than a predetermined number of detected slow waves (six for example). Periods not detected as wake or deep sleep are often flagged as light sleep. Auditory and/or other sensory stimulation may be delivered responsive to deep sleep being continuously detected for at least a threshold amount of time (90 seconds for example), and sleep depth (e.g., indicated by a log-ratio between the delta and beta powers) exceeds a predefined threshold. Auditory stimulation (for example) often includes (e.g., 50-millisecond long) tones separated from each other by a fixed (e.g., one-second long) inter-tone interval. The volume of each tone is linearly modulated by sleep depth such that loud (soft) tones are played during deeper (shallower) sleep. Other stimulation modalities include synchronizing with a slow wave phase and delivering the stimulation in blocks.

Figure 2:
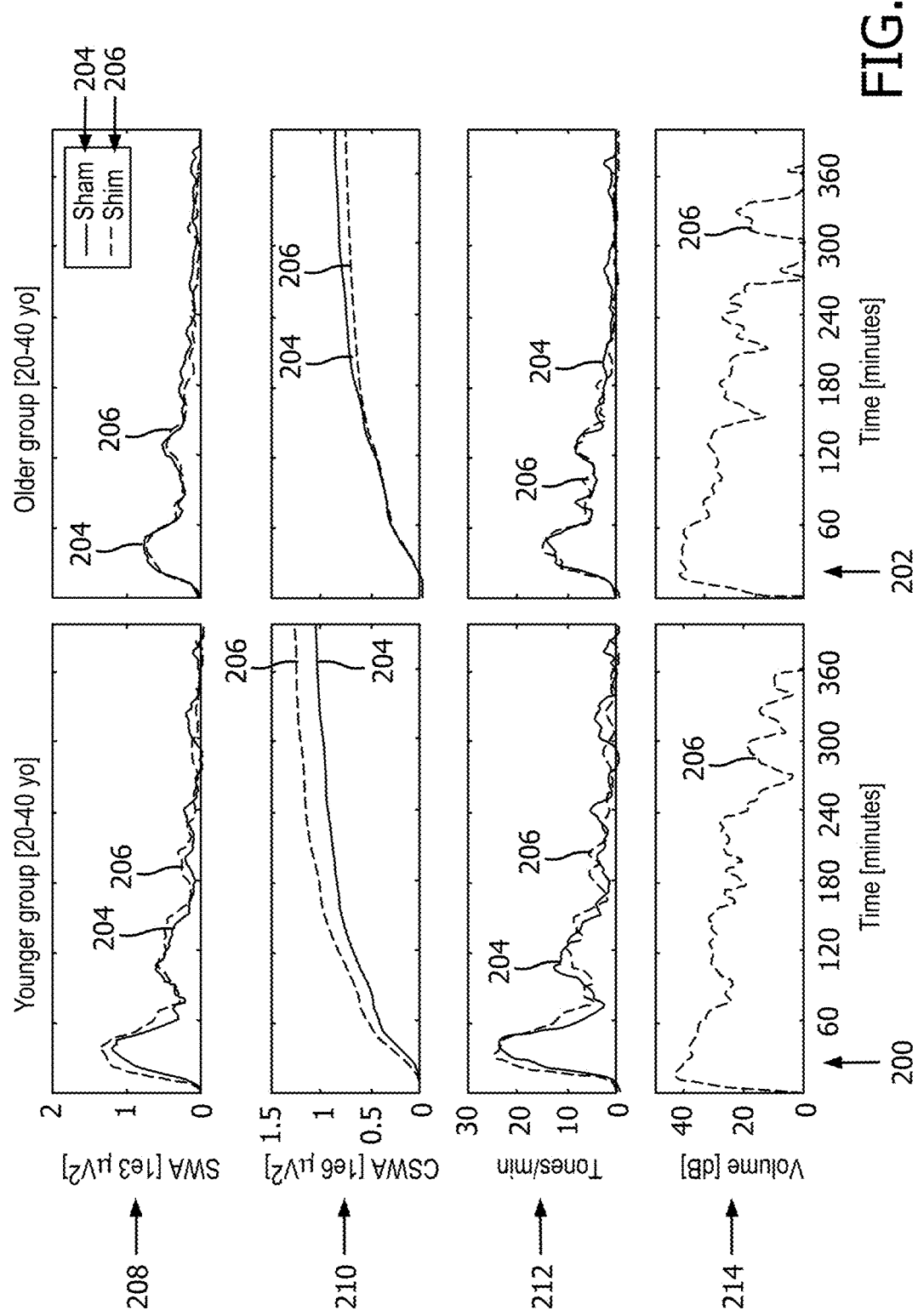
FIG. 2 illustrates the effect of sensory stimulation by prior art systems on a younger demographic group and an older demographic group.

In prior art systems, the effect of stimulation (tones) on slow wave activity enhancement decreases with age. For example, FIG. 2 illustrates the effect of sensory stimulation by prior art systems on a younger demographic group 200 and an older demographic group 202. Sham sleep sessions 204 (where stimulation is not provided) are compared to stimulated sessions 206 for each group. The effect of stimulation from these systems on SWA 208 and CSWA 210 is shown. The average number of tones per unit of time 212, and the average volume in dB 214 are also shown. As shown in FIG. 2, SWA 208, CSWA 210, average number of tones per unit time 212, and average volume 214 are all decreased for older demographic group 202.

Figure 3:
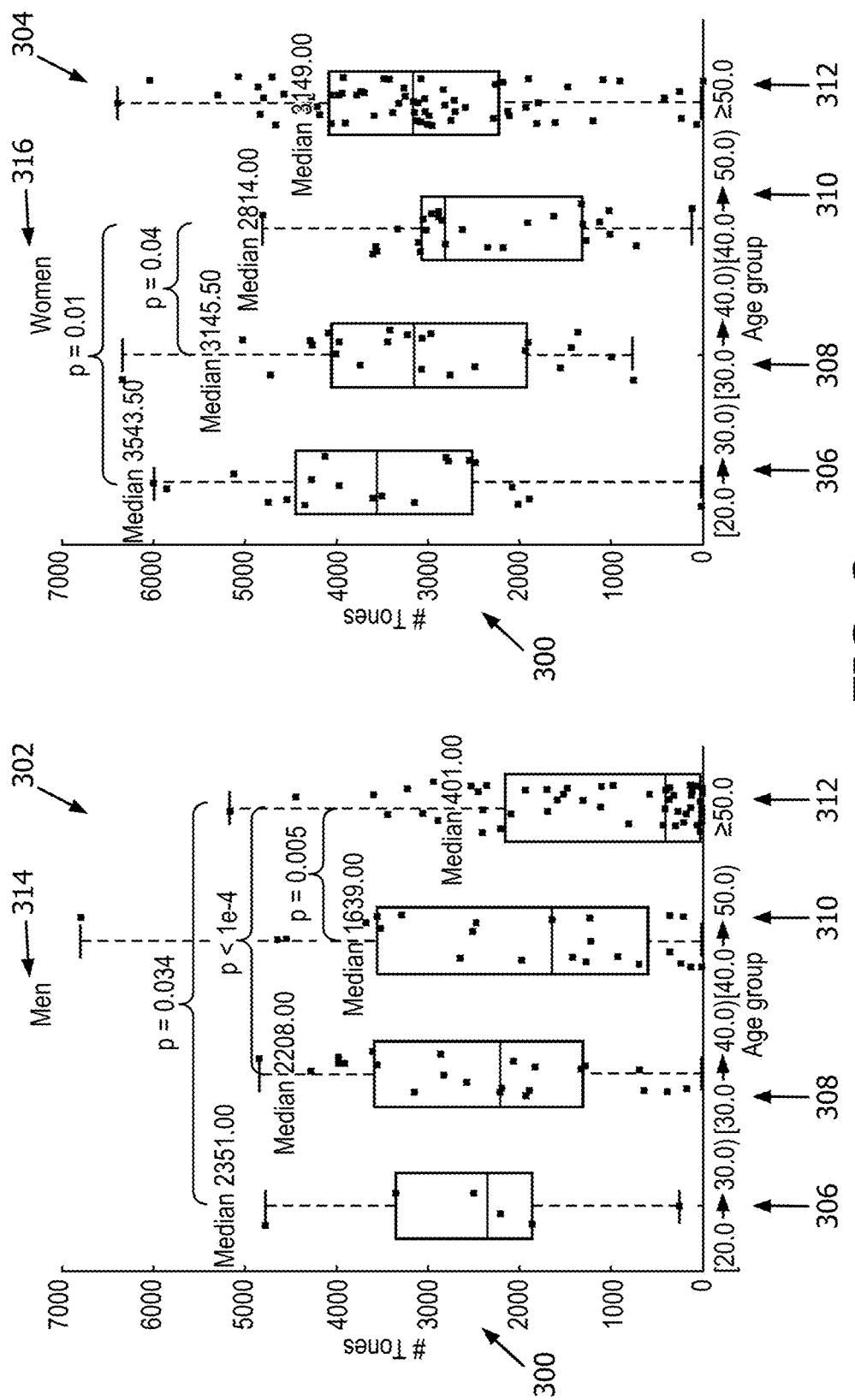
FIG. 3 illustrates the results of an analysis of the number of tones delivered by prior art systems versus various demographic characteristics.

FIG. 3 illustrates the results of an analysis of the number of tones 300 delivered by prior art systems versus various demographic characteristics. Specifically, FIG. 3 illustrates the distribution 302, 304 of the number of tones versus age group (defined in decades in this example) 306, 308, 310, 312, and gender 314, 316. As shown in FIG. 3, the number of tones declines as age increases for both men and women. However, the decline is more pronounced for men. For example, as shown in FIG. 3, the median number of tones for males 50 or older is only 400, which is insufficient to produce CSWA enhancement. In some embodiments, system 10 is configured to reduce or prevent this decrease in stimulation and the ensuing therapy ineffectiveness by adjusting sensory stimulation parameters depending on demographic characteristics of users.

Returning to FIG. 1, in some embodiments, system 10 includes one or more of a sensor 14, a sensory stimulator 16, external resources 18, a processor 20, electronic storage 22, a user interface 24, and/or other components. In some embodiments, system 10 is configured such that user 12 provides demographic information to system 10, for example, using user interface 24. The demographic information may include an age, age range, gender, ethnicity, marital status (e.g., which may guide a volume level so partner disturbance is minimized), work shift (e.g., daytime or nighttime which may be useful to guide volume and timing of the stimulation given circadian factors affecting arousability), and/or other demographic information. The demographic information indicates a demographic group (e.g., age based, gender based, etc.) to which user 12 belongs. The demographic groups may be determined by system 10 based on age, gender, ethnicity, and/or other demographic characteristics. System 10 is configured to select a stimulation parameter model associated with the demographic group of the user from a set of stimulation parameter models associated with different demographic groups. The stimulation parameter models may be stored, for example in electronic storage 22, in external resources 18, and/or in other locations. If demographic information is not provided by user 12, system 10 is configured to determine which demographic group user 12 belongs to automatically. System 10 is configured to control sensory stimulator 16 to deliver the sensory stimulation to the user based on the stimulation parameter model for the demographic group of the user and the output signals from sensor 14 generated during the sleep session. This is further described below.

Sensor 14 is configured to generate output signals conveying information related to brain activity and/or other activity in user 12. In some embodiments, sensor 14 is configured to generate output signals conveying information related to brain activity such as slow wave activity in user 12. In some embodiments, the information related to brain activity and/or other activity in user 12 is the information related to slow wave activity. In some embodiments, sensor 14 is configured to generate output signals conveying information related to stimulation provided to user 12 during sleep sessions. In some embodiments, the information in the output signals from sensor 14 is used to control sensory stimulator 16 to provide sensory stimulation to user 12 (as described below).

Sensor 14 may comprise one or more sensors that generate output signals that convey information related to brain activity in user 12 directly. For example, sensor 14 may include electroencephalogram (EEG) electrodes configured to detect electrical activity along the scalp of user 12 resulting from current flows within the brain of user 12. Sensor 14 may comprise one or more sensors that generate output signals conveying information related to brain activity of user 12 indirectly. For example, one or more sensors 14 may comprise a heart rate sensor that generates an output based on a heart rate of user 12 (e.g., sensor 14 may be a heart rate sensor than can be located on the chest of user 12, and/or be configured as a bracelet on a wrist of user 12, and/or be located on another limb of user 12), movement of user 12 (e.g., sensor 14 may comprise an accelerometer that can be carried on a wearable, such as a bracelet around the wrist and/or ankle of user 12 such that sleep may be analyzed using actigraphy signals), respiration of user 12, and/or other characteristics of user 12.

In some embodiments, sensor 14 may comprise one or more of EEG electrodes, an electrooculogram (EOG) electrode, an actigraphy sensor, an electrocardiogram (EKG) electrode, a respiration sensor, a pressure sensor, a vital signs camera, a photoplethysmogram (PPG) sensor, a functional near infra-red sensor (fNIR), a temperature sensor, a microphone and/or other sensors configured to generate output signals related to the brain activity of user 12 and/or the (e.g., the quantity, frequency, intensity, and/or other characteristics of) stimulation provided to user 12, and/or other sensors. Although sensor 14 is illustrated at a single location near user 12, this is not intended to be limiting. Sensor 14 may include sensors disposed in a plurality of locations, such as for example, within (or in communication with) sensory stimulator 16, coupled (in a removable manner) with clothing of user 12, worn by user 12 (e.g., as a headband, wristband, etc.), positioned to point at user 12 while user 12 sleeps (e.g., a camera that conveys output signals related to movement of user 12), coupled with a bed and/or other furniture where user 12 is sleeping, and/or in other locations.

In FIG. 1, sensor 14, sensory stimulator 16, processor 20, electronic storage 22, and user interface 24 are shown as separate entities. This is not intended to be limiting. Some and/or all of the components of system 10 and/or other components may be grouped into one or more singular devices. For example, these and/or other components may be included in a headset and/or other garments worn by user 12. Such a headset may include, for example, sensing electrodes, a reference electrode, one or more devices associated with an EEG, means to deliver auditory stimulation (e.g., a wired and/or wireless audio device and/or other devices), and one or more audio speakers. In this example, the audio speakers may be located in and/or near the ears of user 12 and/or in other locations. The reference electrode may be located behind the ear of user, and/or in other locations. In this example, the sensing electrodes may be configured to generate output signals conveying information related to brain activity of user 12, and/or other information. The output signals may be transmitted to a processor (e.g., processor 20 shown in FIG. 1), a computing device (e.g., a bedside laptop) which may or may not include the processor, and/or other devices wirelessly and/or via wires. In this example, acoustic stimulation may be delivered to user 12 via the wireless audio device and/or speakers. In this example, the sensing electrodes, the reference electrode, and the EEG devices may be represented, for example, by sensor 14 in FIG. 1. The wireless audio device and the speakers may be represented, for example, by sensory stimulator 16 shown in FIG. 1. In this example, a computing device may include processor 20, electronic storage 22, user interface 24, and/or other components of system 10 shown in FIG. 1.

Sensory stimulator 16 is configured to provide sensory stimulation to user 12. Sensory stimulator 16 is configured to provide auditory, visual, somatosensory, electric, magnetic, and/or other sensory stimulation to user 12 prior to a sleep session, during a sleep session, and/or at other times. In some embodiments, a sleep session may comprise any period of time when user 12 is sleeping and/or attempting to sleep. Sleep sessions may include nights of sleep, naps, and/or other sleeps sessions. For example, sensory stimulator 16 may be configured to provide stimuli to user 12 during a sleep session to facilitate a transition to a deeper stage of sleep, a lighter stage of sleep, maintain sleep in a specific stage, enhance the restorative effects of sleep, and/or for other purposes. In some embodiments, sensory stimulator 16 may be configured such that facilitating a transition between deeper sleep stages and lighter sleep stages includes decreasing sleep slow waves in user 12, and facilitating a transition between lighter sleep stages and deeper sleep stages includes increasing sleep slow waves.

Sensory stimulator 16 is configured to facilitate transitions between sleep stages, maintain sleep in a specific stage, and/or enhance the restorative effects of sleep through non-invasive brain stimulation and/or other methods. Sensory stimulator 16 may be configured to facilitate transitions between sleep stages, maintain sleep in a specific stage, and/or enhance the restorative effects of sleep through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. The sensory stimulation may have an intensity, a timing, and/or other characteristics. For example, acoustic tones may be provided to user 12 to enhance the restorative effects of sleep in user 12. The acoustic tones may include one or more series of tones of a determined length separated from each other by an inter-tone interval. The volume (e.g., the intensity) of individual tones may be modulated based on sleep depth and other factors (as described herein) such that loud tones are played during deeper sleep and soft tones are played during lighter sleep. The length of individual tones (e.g., the timing) and/or the inter tone interval (e.g., the timing) may also be adjusted depending on whether user 12 is in deeper or lighter sleep. This example is not intended to be limiting. Examples of sensory stimulator 16 may include one or more of a sound generator, a speaker, a music player, a tone generator, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to user 12 (e.g., as described below).

External resources 18 include sources of information (e.g., databases, websites, etc.), external entities participating with system 10 (e.g., one or more the external sleep monitoring devices, a medical records system of a health care provider, etc.), and/or other resources. For example, external resources 18 may include sources of historical sleep depth information for a population of users, demographic information for the population of users, and/or other information. The historical sleep depth information for the population of users may be related to brain activity of the population of users that indicates sleep depth over time during sleep sessions of the population of users. In some embodiments, the historical sleep depth information for the population of users may be related to a user population in a given geographical area; demographic information related to gender, ethnicity, age, and/or other demographic information; physiological information (e.g., weight, blood pressure, pulse, etc.) about the population of users, and/or other information. In some embodiments, this information may indicate whether an individual user in the population of user is demographically, physiologically, and/or otherwise similar to user 12.

In some embodiments, external resources 18 include components that facilitate communication of information, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 18 may be provided by resources included in system 10. External resources 18 may be configured to communicate with processor 20, user interface 24, sensor 14, electronic storage 22, sensory stimulator 16, and/or other components of system 10 via wired and/or wireless connections, via a network (e.g., a local area network and/or the internet), via cellular technology, via Wi-Fi technology, and/or via other resources.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The computer program components may comprise one or more of a demographics component 30, a model component 32, an adjustment component 34, a control component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Demographics component 30 is configured to determine a demographic group of user 12. Demographic groups may comprise groups of individuals linked by one or more common demographic characteristics. For example, the demographic groups may comprises groups of individuals having common ages or age ranges, common genders, common ethnicities, and/or other common demographic characteristics. In the description herein, demographic groups are defined by age range. This is an example and is not intended to be limiting. The demographic groups may include any number and type of demographic group that allows system 10 to function as described herein.

In some embodiments, the demographic group of user 12 is determined based on entries and/or selections made by user 12 and/or other users (e.g., caregivers, family members, friends, etc., of user 12). The entries and/or selections may be or be related to demographic characteristics of user 12 and/or other information. The entries and/or selections may be made via user interface 24, for example, and/or via other interfaces. In some embodiments, demographics component 30 is configured to determine the demographic group of user 12 based on information about user 12 stored in electronic storage 22, external resources 18, and/or other sources of information.

In some embodiments, the demographic group of user 12 is determined based on the output signals from sensors 14, the sensory stimulation delivered to user 12, and/or other information. In some embodiments, the demographic group is determined based on the output signals and/or the sensory stimulation generated during a first portion of a sleep session, and/or one or more prior sleep sessions of user 12. In some embodiments, the output signals and/or the sensory stimulation generated during the first portion of the sleep session and/or the prior sleep sessions is used to determine the demographic group for user 12 based on a lack of an explicit demographic group designation for the user (e.g., user 12 did not enter or select any demographic information via user interface 24, or demographics component 30 could not retrieve demographic information for user 12 from electronic storage, etc.).

In some embodiments, determining the demographic group of user 12 based on the output signals from sensors 14, the sensory stimulation delivered to user 12, and/or the other information includes determining one or more sensory stimulation parameters of the sensory stimulation delivered to user 12. For example, if the demographic group of user 12 is unknown, control component 36 (described below) may cause sensory stimulators 16 to deliver the sensory stimulation based on the output signals from sensor 14 according to a predetermined therapy plan (e.g., a baseline or standard therapy plan). The sensory stimulation parameters for the resulting sensory stimulation delivered to user 12 may be compared to known sensory stimulation parameters for various demographic groups who have undergone therapy according to the same predetermined therapy plan. User 12 may be determined to belong to a specific demographic group responsive to the sensory stimulation parameters of the sensory stimulation delivered to user 12 being similar to and/or the same as the sensory stimulation parameters of sensory stimulation typically delivered to users from a specific demographic group. For example, if sensory stimulator 16 is or includes a tone generator, the sensory stimulation parameters may include an intensity, a frequency, a timing, a duration, a quantity, and/or other characteristics of auditory tones delivered user 12 and/or other users.

In some embodiments, determining the demographic group of user 12 based on the output signals from sensors 14, the sensory stimulation delivered to user 12, and/or the other information includes determining one or more brain activity parameters of user 12. The brain activity parameter for user 12 may be compared to known brain activity parameters typical for individuals from various demographic groups undergoing sleep therapy. As described above, if the demographic group of user 12 is unknown, control component 36 (described below) may cause sensory stimulators 16 to deliver the sensory stimulation based on the output signals from sensor 14 according to a predetermined therapy plan (e.g., a baseline or standard therapy plan). User 12 may be determined to belong to a specific demographic group responsive to the brain activity parameters of user 12 being similar to and/or the same as the brain activity parameters of a specific demographic group who have undergone therapy with the same predetermined therapy plan. The brain activity parameters may be determined by demographics component 30 based on the output signals from sensor 14 and/or other information. The brain activity parameters may indicate depth of sleep in the user and/or other information. In some embodiments, the information in the output signals related to brain activity indicates sleep depth over time. In some embodiments, the information indicating sleep depth over time is or includes information related to slow wave activity in user 12. In some embodiments, the slow wave activity of user 12 may be indicative of sleep stages of user 12. The sleep stages of user 12 may be associated with rapid eye movement (REM) sleep, non-rapid eye movement (NREM) sleep, and/or other sleep. The sleep stages may be one or more of NREM stage N1, stage N2, or stage N3, REM sleep, and/or other sleep stages. In some embodiments, the sleep stages of user 12 may be one or more of stage S1, S2, S3, or S4. In some embodiments, NREM stage 2 and/or 3 (and/or S3 and/or S4) may be slow wave (e.g., deep) sleep. In some embodiments, the information related to brain activity that indicates sleep depth over time is and/or is related to one or more additional brain activity parameters.

In some embodiments, the information related to brain activity that indicates sleep depth over time is and/or includes EEG information generated during one or more sleep sessions. In some embodiments, brain activity parameters may be determined based on the EEG information. In some embodiments, the brain activity parameters may be previously determined and be part of historical sleep depth information obtained from external resources 18. In some embodiments, the brain activity parameters are and/or are related to a frequency, amplitude, phase, presence of specific sleep patterns such as spindles, K-complexes, or sleep slow waves, alpha waves, and/or other characteristics of an EEG signal. In some embodiments, the brain activity parameters are determined based on the frequency, amplitude, and/or other characteristics of the EEG signal. In some embodiments, the determined brain activity parameters and/or the characteristics of the EEG may be and/or indicate sleep stages that correspond to the REM and/or NREM sleep stages described above. For example, typical EEG characteristics during NREM sleep include a transition from alpha waves (e.g., about 8-12 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 4 Hz), also known as sleep slow waves, with peak-to-peak amplitudes greater than about 75 uV for sleep stage N3; presence of light sleep and/or arousals, and/or other characteristics. In some embodiments, light sleep may be characterized by the fact that the alpha activity (e.g., EEG power in the 8-12 Hz band) is no longer present and slow waves are not present. In some embodiments, slow wave activity is a continuous value (e.g., EEG power in the 0.4 to 4 Hz band), which is positive. In some embodiments, an absence of slow waves is indicative of light sleep. In addition, spindle activity (EEG power in the 11 to 16 Hz band) may be high. Deep sleep may be characterized by the fact that delta activity (e.g., EEG power in the 0.5 to 4 Hz band) is dominant. In some embodiments, EEG power in the delta band and SWA are the same when considering sleep EEG. In some embodiments, the information related to brain activity that indicates sleep depth over time indicates changes in an EEG delta power over time, a quantity of micro arousals in the population of users, other EEG power levels, and/or other parameters.

Model component 32 is configured to select a stimulation parameter model associated with the demographic group of user 12. The selection of the stimulation parameter is made based on the determination by demographics component 30 of which demographic group user 12 belongs to, and/or other information. The stimulation parameter model is selected from a set of stimulation parameter models associated with different demographic groups (e.g., different age ranges). The stimulation parameter models may be stored, for example in electronic storage 22, in external resources 18, and/or in other locations. Once the stimulation parameter model associated with the demographic group of user 12 is selected, control component 36 (described below) is configured to control stimulator 16 to deliver sensory stimulation to user 12 based on the selected model.

Figure 4:
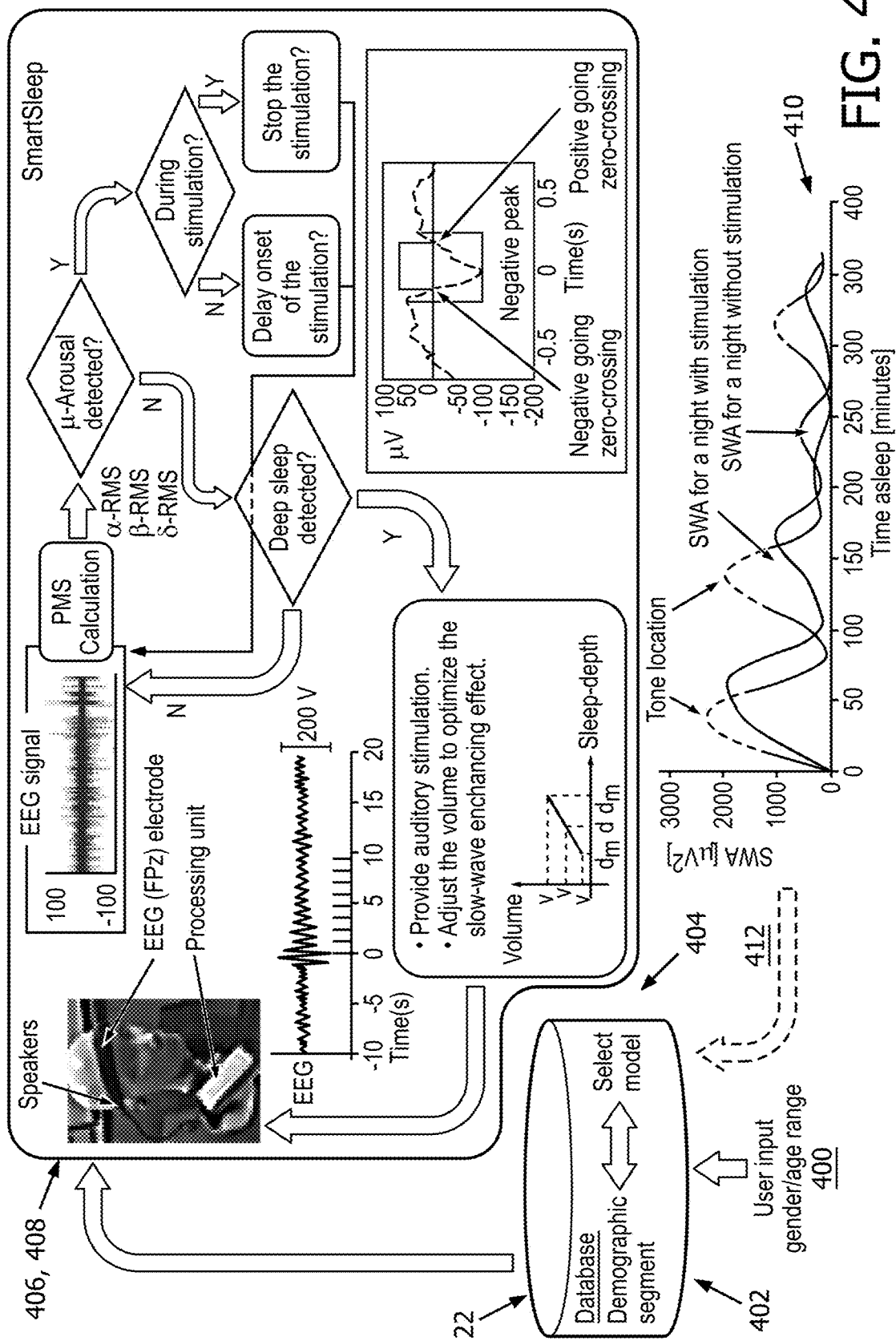
FIG. 4 illustrates operations performed by a demographics component, a model component, and a control component of the system, in accordance with one or more embodiments.

Operations performed by demographics component 30, model component 32, and control component 36 are illustrated in FIG. 4. As shown in FIG. 4, demographics component 30 (FIG. 1) may facilitate input 400 of a user's gender and age range (for example). Demographics component 30 may determine the demographic group to which the user belongs 402, and model component 32 (FIG. 1) may select the appropriate stimulation parameter model from electronic storage 22 and/or other sources of information. Once the stimulation parameter model associated with the demographic group of the user is selected, control component 36 (FIG. 1) is configured to control 406 delivery of sensory stimulation to the user based on the selected model. However, if the demographic group of the user is unknown, control component 36 may cause delivery 408 of the sensory stimulation based on sensor (e.g., sensor 14 shown in FIG. 1) output signals according to a predetermined therapy plan (e.g., a baseline or standard therapy plan). The user may be determined 410, 412 to belong to a specific demographic group responsive to the brain activity parameters of the user or the parameters of the sensory stimulation delivered to the user being similar to and/or the same as the brain activity parameters and/or the sensory stimulation parameters of a specific demographic group who have undergone therapy with the same predetermined therapy plan.

Returning to FIG. 1, the stimulation parameter models may be and/or indicate a relationship between one or more stimulation control parameters and a target variable for the sensory stimulation. Stimulation control parameters may be one or more tunable parameters that may be used to control sensory stimulation delivered to user 12. In some embodiments, the stimulation parameter models may be thought of as being similar to recipes for use in setting the stimulation control parameters when delivering sensory stimulation to a user. The stimulation control parameters used in a model may be stimulation control parameters that have a relatively larger influence on the target variable compared to other stimulation control parameters. The stimulation control parameters used in a model may be the same or different for individual demographic groups. A given model may change (e.g., the stimulation control parameters used in the model may change, the relationship between the stimulation control parameters may change, etc.) depending on the target variable for the sensory stimulation. A target variable may be a variable that model component 32 and/or adjustment component 34 are configured to enhance for user 12. The target variable may be determined by model component 32 and/or adjustment component 34 based on information from previous sleep sessions for user 12 or users demographically similar to user 12, may be determined at manufacture of system 10, may be entered and/or selected (e.g., via user interface 24) by user 12 and/or other users, and/or may be determined in other ways. In some embodiments, the target variable may be a number of tones delivered to user 12 (e.g., because the number of tones is known to decrease with age in prior art systems as described above). In some embodiments, the target variable may be one or more target variables. For example, the target variable may be one or more of the number of tones delivered to user 12, an amount of detected N3 sleep, average N3 duration, detected N1 and/or N2 sleep duration, N3 sensitivity and/or specificity, Kappa, wake sensitivity and/or specificity, duration of wake detected as N3, REM detection sensitivity and/or specificity, sleep efficiency (e.g., time asleep divided by the time in bed), sleep maintenance (e.g., sleep bout duration), and/or other target variables. (A sleep bout is a continuous period of sleep (N1, N2, N3, or REM) not interrupted by wakefulness.) The relationships between the target variables, and the stimulation control parameters in a model may be linear or non-linear. Individual stimulation control parameters may be weighted or non-weighted.

Adjustment component 34 is configured to determine and/or adjust the stimulation parameter models in the set of stimulation parameter models. In some embodiments, determining and/or adjusting the simulation parameter models includes obtaining historical brain activity information for a population of users in a given demographic group. As described above, the historical brain activity information indicates sleep depth over time during sleep sessions of the population of users. Determining and/or adjusting the stimulation parameter models includes performing simulations of sensory stimulation for users in a particular demographic group based on (i) the historical brain activity information for the users in that demographic group, and (ii) one or more stimulation control parameters. Determining and/or adjusting the stimulation parameter models includes adjusting, at multiple times during each of the simulations, the stimulation control parameters such that the simulation is performed based on the stimulation control parameters as adjusted at the multiple times. This includes determining, with respect to each of the adjustments, an effect of the adjustment of the stimulation control parameters on a target variable. Based on the effects of the adjustments, adjustment component 34 is configured to determine a set of stimulation control parameters for a given stimulation parameter model associated with the given demographic group. Individual determined and/or adjusted stimulation parameter models are stored as part of the set of stimulation parameter models.

In some embodiments, adjustment component 34 is configured such that determining and/or adjusting the stimulation parameter models in the set of stimulation parameter models comprises determining which stimulation control parameters have more influence on the target variable relative to other stimulation control parameters. Adjustment component 34 may be configured to determine and/or adjust individual stimulation parameter models based on the stimulation control parameters with relatively more influence on the target variable. In some embodiments, the stimulation control parameters with relatively more influence on the target outcome variable comprise a delta threshold, a slow wave peak threshold, a slow wave density threshold, a sleep depth threshold, and/or other stimulation control parameters. In some embodiments, for example, the sensory stimulators comprise a tone generator, and the target variable comprises a number of tones that would be delivered during simulated sleep sessions.

By way of a non-limiting example, the stimulation control parameters with relatively more influence on the number of tones that would be delivered to user 12 may include a delta threshold on the RMS power in the delta (0.5 to 4 Hz) band above which N3 sleep can be detected, a slow wave peak threshold on the negative peaks of potential slow wave events in order to be detected as actual slow waves, a slow wave density threshold on the minimum number of detected slow wave events to transition to N3 sleep, and a sleep depth threshold on the log-ratio delta/beta which characterizes sleep depth above which stimulation can be delivered. In this example, demographic groups are defined as men and then women in age groups 20-40, 40-50, and 50+ years old. These groups should not be considered limiting. For example, differences within narrower age group ranges may be identified, and/or age may be used as a continuous variable.

As described above, a model is determined for each demographic group. The model characterizes the number of tones (the target variable in this example) based on configurable (stimulation control) parameters. The number of tones is an example of a target variable (outcome) that may be modeled. Examples of other target variables include SWA, CSWA, and/or other sleep architecture outcomes (e.g. the duration of N3 sleep) as described above.

Figure 5:
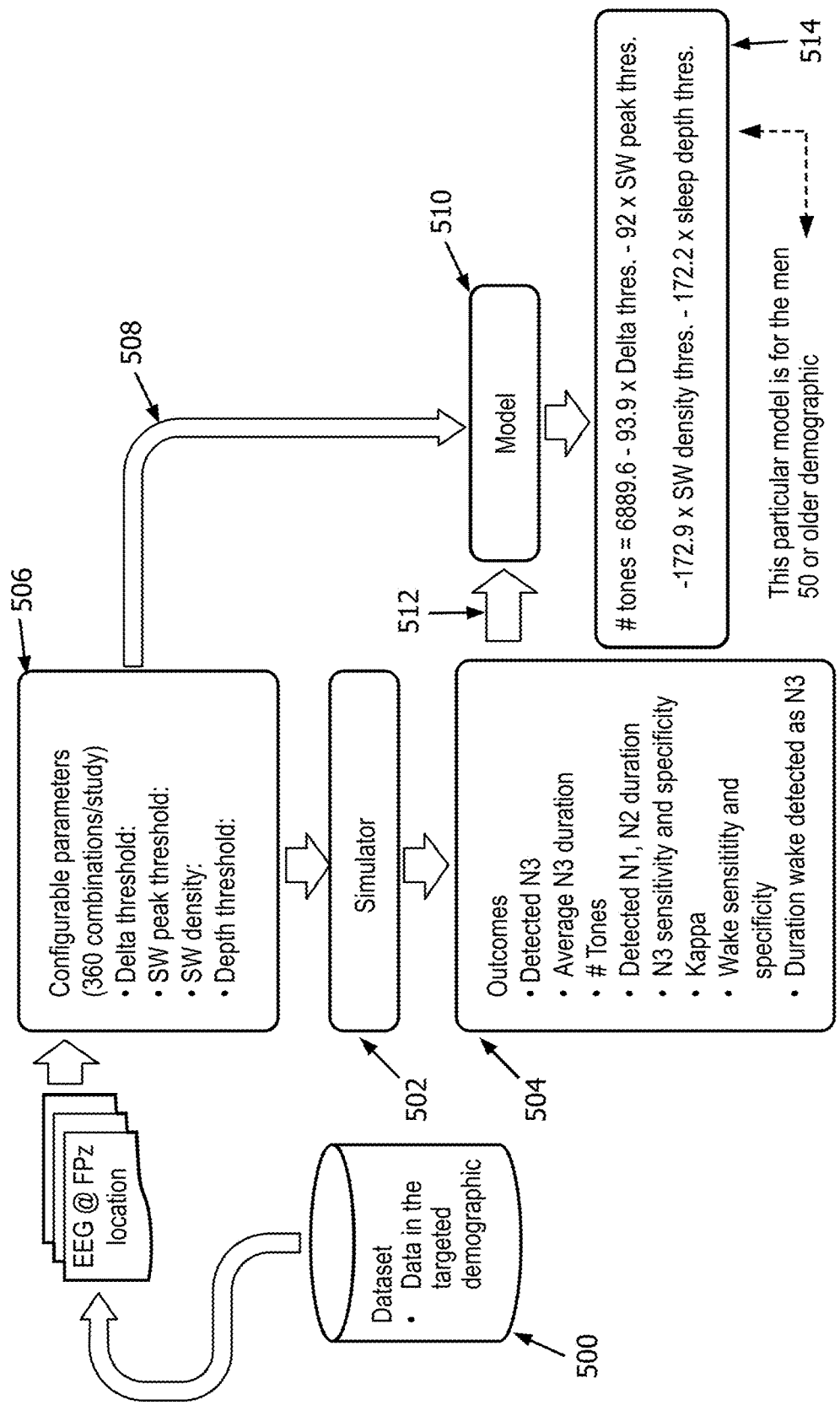
FIG. 5 illustrates a process for determining and/or adjusting stimulation parameter models by performing simulations of sensory stimulation for users in a particular demographic group, in accordance with one or more embodiments.

Continuing with this example, the process for determining and/or adjusting the stimulation parameter models by performing simulations of sensory stimulation for users in a particular demographic group is illustrated in FIG. 5. As shown in FIG. 5 sleep EEG data from subjects in a targeted demographic group 500 are processed through a simulator 502 (e.g., adjustment component 34 shown in FIG. 1) which determines outcomes 504 (e.g., a number of tones and other target variables as shown in FIG. 5) depending on different combinations of the configurable (stimulation control) parameters 506. Configurable parameters 506 are provided 508 as potential components of a model 510. Configurable (stimulation control) parameters 506 with more influence on outcomes 504 (target variables) relative to other configurable parameters 506 are identified based on the simulations and used 512 as part of model 510. In this example, the number of tones (target variable) in the demographic group of men 50 years old or older may be modeled by a mixed effects model as shown in the bottom right section 514 of FIG. 5. This model provides an estimation of the change in stimulation (e.g., delivered tones) responsive to changes in relatively more influential configurable (stimulation control) parameters. For example, a reduction of a unit in the delta threshold may increase the stimulation by 93.9 tones on average. More complex models (e.g. non-linear models) than the one portrayed in FIG. 5 are contemplated. However, linear approximations around specific points may be constructed using local derivatives.

For example, the points may correspond to default parameters. By way of illustration, this means:

$$A \text{ target variable} \sim T0 + \frac{\partial T}{\partial x}(x - x0) + \frac{\partial T}{\partial y}(y - y0) + \frac{\partial T}{\partial z}(z - z0) + \frac{\partial T}{\partial u}(u - u0)$$

If the target variable T is the number of tones:
x is the delta threshold, x0=10 (for example); y is the SW peak threshold, y0=29 (for example); z is the SW density threshold, z0=6 (for example); u is the sleep depth threshold, u0=5 (for example); and: $\delta T/\delta x$ is the partial derivative of T with w, r, t, and x evaluated at x0; $\delta T/\delta y$ is the partial derivative of T with w, r, t, and y evaluated at y0; $\delta T/\delta z$ is the partial derivative of T with w, r, t, and z evaluated at z0; and $\delta T/\delta u$ is the partial derivative of T with w, r, t, and u evaluated at u0.

In some embodiments, determining and/or adjusting a model (e.g., operations performed by adjustment component 34 shown in FIG. 1) may include making stimulation control parameter changes with respect to default values for the stimulation control parameters. Adjustment component 34 is configured to change those stimulation control parameters for which a small variation (e.g. a single unit) causes a relatively large effect on the outcome (target variable). Using the men 50 years old or older demographic and the model 510, 514 in FIG. 5, a unit change in either (i) sleep depth threshold (e.g., having a weighting or multiplier of 172.2 in the model) or (ii) slow wave density threshold (e.g., having a weighting or multiplier of 172.9) causes approximately twice the effect of (iii) a unit change in the slow wave peak threshold (i.e., having a weighting or multiplier of 92) or (iv) delta threshold (i.e., having a weighting or multiplier of 93.9).

Figure 6:
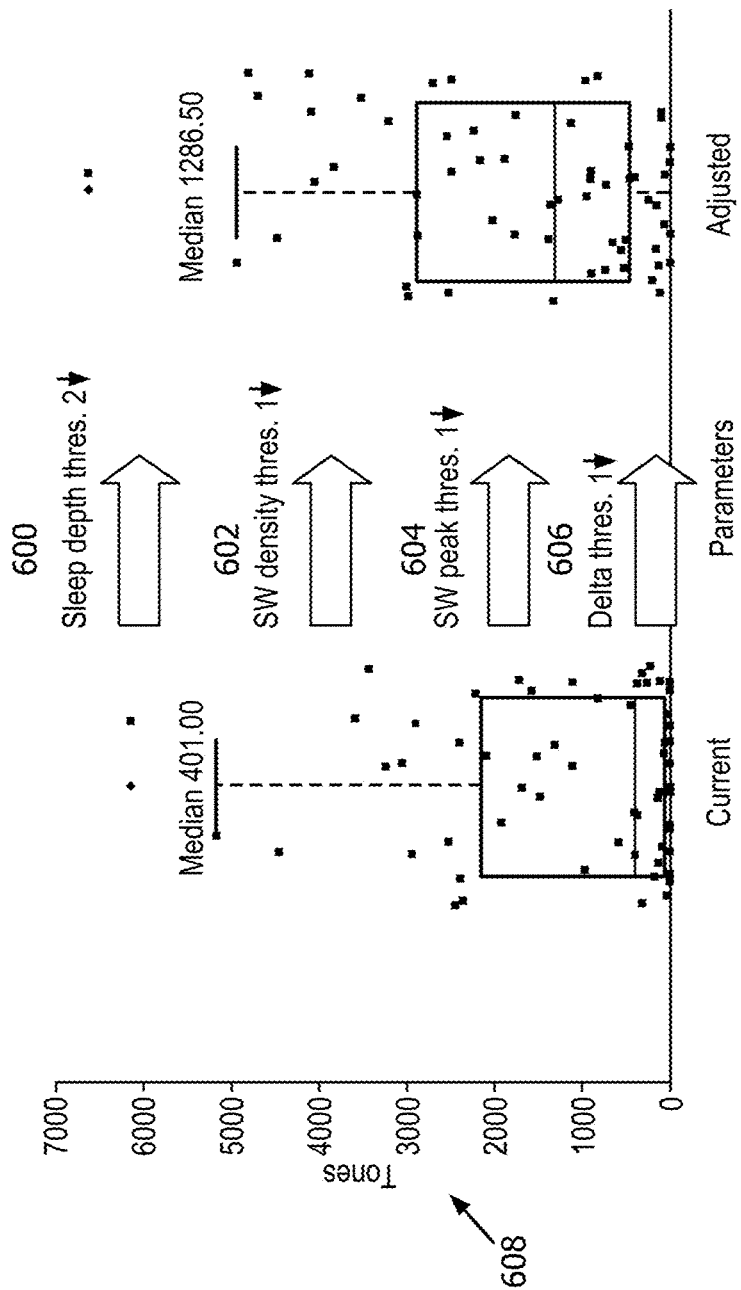
FIG. 6 illustrates an example optimization of stimulation control parameter values for a demographic stimulation parameter model, in accordance with one or more embodiments.

FIG. 6 illustrates an example optimization of stimulation control parameter values for the male 50 or older demographic stimulation parameter model (as one example). Reducing 600 the sleep depth threshold by two units with respect to a default or otherwise previously set parameter value, reducing 602 the slow wave density threshold by one unit, reducing 604 the slow wave peak threshold by one unit, and reducing 606 the delta power threshold by one unit, causes the median number of tones 608 in this demographic to increase from 400 to close to 1300. As the above example demonstrates, for a single target variable (outcome), the stimulation control parameter values ensuring a maximum (or minimum, optimized, etc.) level for that demographic group may be readily determined. In some embodiments, adjustment component 34 (FIG. 1) is configured to determine and/or adjust a model based on multiple target variables (outcomes). In some embodiments, this may include optimizing a linear combination of the target variables (outcomes), establishing rules for individual target variables (outcomes), and/or other operations. To better understand optimization, suppose that we want to maximize both N3 sensitivity and N3 specificity but we give higher weight to sensitivity, one could consider as a target the following linear combination: T=λ*N3 sensitivity+(1−λ)*N3 specificity, with λ=0.8. Simultaneously minimizing and maximizing is possible by considering subtractions, for example. In the example described above, where the number of tones was chosen as the target variable (outcome), adjustment component 34 would select the sleep depth, slow wave density, slow wave peak, and delta thresholds corresponding to the maximum number of tones estimated through simulation. For example, if N3 sensitivity and specificity are selected as combined target variables (outcomes), adjustment component 34 would select the sleep depth, slow wave density, slow wave peak, and delta thresholds achieving maximum accuracy as defined by their linear combination accuracy=weight1*N3 sensitivity+ weight2*N3 specificity. If both N3 sensitivity and N3 specificity need to be maximized, system 10 may be configured such that one should select (or system 10 should set) weight1 and weight 2 to be positive, for example. In a rule based embodiment, adjustment component 34 would select any combination of parameters that exceed a predefined threshold for the target variable (outcome) (e.g., N3 sensitivity>0.9 and N3 specificity>0.8).

In some embodiments, given demographic information and a minimum desired value of a target variable (outcome), stimulation control parameter values may be determined and/or adjusted differently. In the example above, adjustment component 34 would change the stimulation control parameters not to the values that give a maximum number of tones, but to stimulation control parameter values that achieve a minimum desired number of tones, e.g. 1000 tones. This embodiment may be useful in cases where extensive testing was done to define a generic (default) parameter set and adjustment component 34 is configured to deviate as little as possible from the generic parameter set so as not to affect (or minimally affect) other target variables not considered during the determination and/or adjustment of a model.

Returning to FIG. 1, control component 36 is configured to cause sensory stimulators 16 to deliver the sensory stimulation. Control component 36 causes the sensory stimulation to be delivered based on the output signals, the stimulation parameter model for the demographic group of user 12, and/or other information. For example, if the demographic group of user 12 is unknown, control component 36 may cause sensory stimulators 16 to deliver the sensory stimulation based on the output signals from sensory stimulator 16 according to a predetermined therapy plan. This may occur, for example, during a first portion of a sleep session. This may also occur during one or more previous sleep sessions. One of these previous sleep sessions may be a calibration sleep session, for example, or other sleep sessions. This means this type of stimulation may be delivered altogether before a current sleep session, in some embodiments. If the demographic group of user 12 is known and/or is determined and/or adjusted by system 10 as described above, control component 36 is configured to cause sensory stimulators 16 to deliver the sensory stimulation based on the stimulation parameter model for the demographic group of user 12. In some embodiments, the sensory stimulation is delivered based on the stimulation parameter model for the demographic group of the user and the output signals generated during a second portion of a sleep session (e.g., subsequent to the first portion of the sleep session). However, in some embodiments, if the stimulation was delivered according to the predetermined therapy plan during one or more previous sleep sessions such as a calibration session, etc., control component 36 may cause sensory stimulator 16 to deliver the stimulation based on the stimulation parameter model for the demographic group of user 12 directly from the start of a current sleep session (e.g., not just during a second portion of the sleep session).

Control component 36 is configured to control stimulator 16 to provide stimulation to user 12 according to the predetermined therapy plan and/or based on the stimulation parameter model for the demographic group of user 12 during sleep and/or at other times. Control component 36 is configured to cause sensory stimulator 16 to provide sensory stimulation to user 12 based on the sleep stage of user 12, and/or other information. Control component 36 is configured to cause sensory stimulator 16 to provide the sensory stimulation to user 12 based on the sleep stage and/or other information over time during the sleep session (e.g., according to the predetermined therapy plan, the stimulation parameter model, and/or other information). Control component 36 is configured to cause sensory stimulator 16 to provide sensory stimulation to user 12 responsive to user 12 being in, or likely being in, deep enough sleep for stimulation (e.g., deep (N3) sleep).

In some embodiments, stimulators 16 are controlled by control component 36 to enhance sleep slow waves through (e.g. peripheral auditory, magnetic, electrical, and/or other) stimulation delivered in NREM sleep (as described herein). In some embodiments, control component 36 (and/or one or more of the other processor components described herein) performs one or more operations similar to and/or the same as the operations described in U.S. patent application Ser. No. 14/784,782 (entitled "System and Method for Sleep Session Management Based on Slow Wave Sleep Activity in a Subject"), Ser. No. 14/783,114 (entitled "System and Method for Enhancing Sleep Slow Wave Activity Based on Cardiac Activity"), Ser. No. 14/784,746 (entitled "Adjustment of Sensory Stimulation Intensity to Enhance Sleep Slow Wave Activity"), Ser. No. 15/101,008 (entitled "System and Method for Determining Sleep Stage Based on Sleep Cycle"), and/or Ser. No. 15/100,435 (entitled "System and Method for Facilitating Sleep Stage Transitions"), which are all individually incorporated by reference in their entireties.

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 22 may store software algorithms, information determined by processor 20, information received via user interface 24 and/or external computing systems (e.g., external resources 18), and/or other information that enables system 10 to function as described herein. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and user 12, and/or other users through which user 12 and/or other users may provide information to and receive information from system 10. This enables data, cues, results, and/or instructions and any other communicable items, collectively referred to as "information," to be communicated between a user (e.g., user 12) and one or more of sensor 14, sensory stimulator 16, external resources 18, processor 20, and/or other components of system 10. For example, a hypnogram, EEG data, and/or other information may be displayed for user 12 or other users via user interface 24. As another example, user 12 may enter and/or select demographic information via user interface 24. User interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10.

Figure 7:
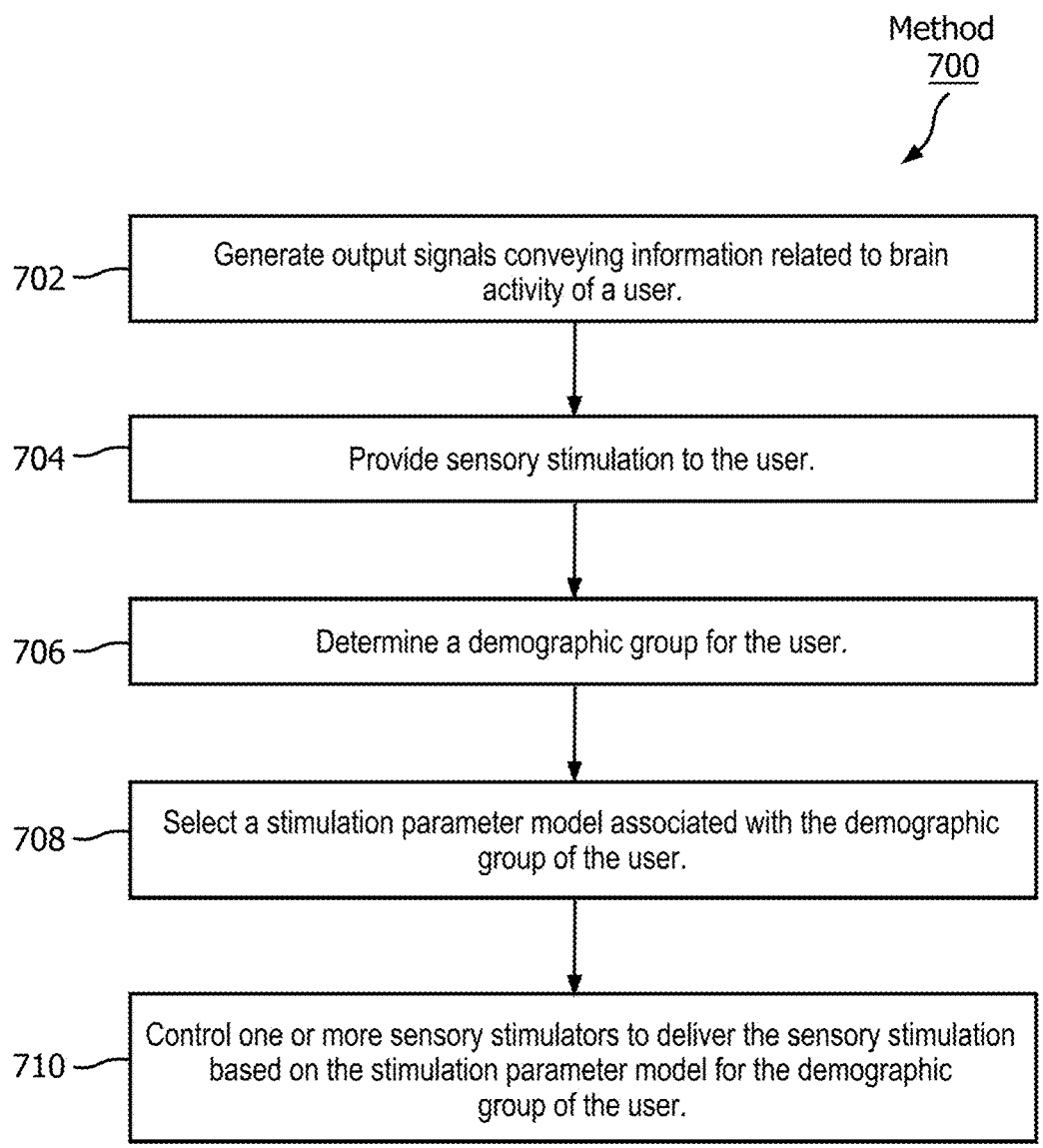
FIG. 7 illustrates a method for delivering sensory stimulation to a user during a sleep session, in accordance with one or more embodiments.

FIG. 7 illustrates method 700 for delivering sensory stimulation to a user with a delivery system. The system comprises one or more sensors, one or more sensory stimulators, one or more processors configured by machine-readable instructions, and/or other components. The processors are configured to execute computer program components. The computer program components comprise a demographics component, a model component, an adjustment component, a control component, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices such as one or more processors 20 described herein (e.g., a digital processor, an analog processor, a digital circuit designed to process information, an analog circuit designed to process information, a state machine, and/or other mechanisms for electronically processing information). The processing devices may include one or more devices executing some or all of the operations of method 700 in response to instructions stored electronically on an electronic storage medium. The processing devices may include one or more devices configured through hardware, firmware, and/or software to be specifically designed for execution of one or more of the operations of method 700.

At an operation 702, output signals conveying information related to brain activity of a user during a sleep session are generated. In some embodiments, operation 702 is performed by one or more sensors the same as or similar to sensors 14 (shown in FIG. 1 and described herein).

At an operation 704, sensory stimulation is provided to the user during the sleep session. In some embodiments, the sensory stimulation is provided to the user during a first portion of the sleep session (e.g., or a wholly earlier sleep session) based on output signals generated during the first portion of the sleep session (or the earlier sleep session). In some embodiments, operation 704 is performed by one or more sensory stimulators the same as or similar to sensory stimulators 16 (shown in FIG. 1 and described herein).

At an operation 706, a demographic group of the user is determined. The demographic group is determined based on the output signals. In some embodiments, the demographic group is determined based on the output signals generated during the first portion of the sleep session (or the earlier sleep session). In some embodiments, the demographic group is determined based on the sensory stimulation that is delivered during the first portion of the sleep session (or the earlier sleep session). In some embodiments, operation 706 includes using the output signals generated during the first portion of the sleep session (or the earlier sleep session) to determine the demographic group for the user based on a lack of an explicit demographic group designation for the user. In some embodiments, operation 706 is performed by a processor component the same as or similar to demographics component 30 (shown in FIG. 1 and described herein).

At an operation 708, a stimulation parameter model associated with the demographic group of the user is selected. The stimulation parameter model is selected from a set of stimulation parameter models associated with different demographic groups. In some embodiments, operation 708 includes determining and/or adjusting the stimulation parameter model in the set of stimulation parameter models. For example, in some embodiments, operation 708 includes obtaining historical brain activity information for a population of users in a given demographic group. The historical brain activity information indicates sleep depth over time during sleep sessions of the population of users. Operation 708 includes performing simulations of sensory stimulation based on (i) the historical brain activity information and (ii) one or more stimulation control parameters. Operation 708 includes adjusting, at multiple times during each of the simulations, the one or more stimulation control parameters such that the simulation is performed based on the one or more stimulation control parameters as adjusted at the multiple times. Operation 708 includes determining, with respect to each of the adjustments, an effect of the adjustment of the one or more stimulation control parameters on a target variable. Operation 708 includes determining, based on the effects of the adjustments, a set of stimulation control parameters for a given stimulation parameter model associated with the given demographic group. Operation 708 includes storing the given stimulation parameter model as part of the set of stimulation parameter models. In some embodiments, for example, the one or more sensory stimulators comprise a tone generator, and the target variable comprises a number of tones that would be delivered during simulated sleep sessions. In some embodiments, operation 708 is performed by processor components the same as or similar to model component 32 and/or adjustment component 34 (shown in FIG. 1 and described herein).

At an operation 710, the one or more sensory stimulators are controlled to deliver the sensory stimulation based on the stimulation parameter model for the demographic group of the user. In some embodiments, the sensory stimulation is delivered based on the stimulation parameter model for the demographic group of the user and the output signals generated during a second portion of the sleep session (e.g., or a wholly later sleep session). In some embodiments, this stimulation is delivered during the second portion of the sleep session (or a later sleep session). The second portion of the sleep session (or the second sleep session) is subsequent to the first portion of the sleep session (or the first sleep session). In some embodiments, operation 710 is performed by a processor component the same as or similar to control component 36 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to deliver sensory stimulation to a user during a sleep session, the system comprising:
    one or more sensors configured to generate output signals conveying information related to brain activity of the user during the sleep session;
    one or more sensory stimulators configured to provide the sensory stimulation to the user during the sleep session; and
    one or more processors coupled to the one or more sensors and the one or more sensory stimulators, the one or more processors configured by machine-readable instructions to:
        determine a demographic group for the user based on the output signals generated during a first portion of the sleep session;
        select, during the sleep session, a stimulation parameter model associated with the demographic group of the user from a set of stimulation parameter models associated with different demographic groups;
        control, during a second portion of the sleep session, the one or more sensory stimulators to deliver the sensory stimulation to the user based on the stimulation parameter model for the demographic group of the user and the output signals generated during the second portion of the sleep session, the second portion of the sleep session being subsequent in time to the first portion of the sleep session
        obtain historical brain activity information for a population of users in a given demographic group, the historical brain activity information indicating sleep depth over time during sleep sessions of the population of users;
        perform simulations of sensory stimulation based on (i) the historical brain activity information and (ii) one or more stimulation control parameters;
        adjust, at multiple times during each of the simulations, the one or more stimulation control parameters such that the simulation is performed based on the one or more stimulation control parameters as adjusted at the multiple times;
        determine, with respect to each of the adjustments, an effect of the adjustment of the one or more stimulation control parameters on a target variable;
        determine, based on the effects of the adjustments, a set of stimulation control parameters for a given stimulation parameter model associated with the given demographic group; and
        store the given stimulation parameter model as part of the set of stimulation parameter models.

2. The system of claim 1, wherein the one or more processors are further configured to:
    control, during the first portion of the sleep session, the one or more sensory stimulators to deliver the sensory stimulation based on the output signals generated during the first portion of the sleep session; and
    determine the demographic group for the user based on the sensory stimulation that is delivered during the first portion of the sleep session.

3. The system of claim 1, wherein the one or more processors are configured to use the output signals generated during the first portion of the sleep session to determine the demographic group for the user based on a lack of an explicit demographic group designation for the user.

4. The system of claim 1, wherein the one or more sensory stimulators comprise a tone generator, and wherein the one or more processors are configured such that the target variable comprises a number of tones that would be delivered during simulated sleep sessions.

5. A method for delivering sensory stimulation to a user during a sleep session with a delivery system, the system comprising one or more sensors, one or more sensory stimulators, and one or more processors, the method comprising:
    generating, with the one or more sensors, output signals conveying information related to brain activity of the user during the sleep session;
    providing, with the one or more sensory stimulators, the sensory stimulation to the user during the sleep session;
    determining, with the one or more processors, a demographic group for the user based on the output signals generated during a first portion of the sleep session;
    selecting, with the one or more processors, during the sleep session, a stimulation parameter model associated with the demographic group of the user from a set of stimulation parameter models associated with different demographic groups;
    controlling, with the one or more processors, during a second portion of the sleep session, the one or more sensory stimulators to deliver the sensory stimulation to the user based on the stimulation parameter model for the demographic group of the user and the output signals generated during the second portion of the sleep session, the second portion of the sleep session being subsequent in time to the first portion of the sleep session;
    obtaining, with the one or more processors, historical brain activity information for a population of users in a given demographic group, the historical brain activity information indicating sleep depth over time during sleep sessions of the population of users;
    performing, with the one or more processors, simulations of sensory stimulation based on (i) the historical brain activity information and (ii) one or more stimulation control parameters;
    adjusting, with the one or more processors, at multiple times during each of the simulations, the one or more stimulation control parameters such that the simulation is performed based on the one or more stimulation control parameters as adjusted at the multiple times;

determining, with the one or more processors, with respect to each of the adjustments, an effect of the adjustment of the one or more stimulation control parameters on a target variable;

determining, with the one or more processors, based on the effects of the adjustments, a set of stimulation control parameters for a given stimulation parameter model associated with the given demographic group; and storing, with the one or more processors, the given stimulation parameter model as part of the set of stimulation parameter models.

6. The method of claim 5, further comprising:

controlling, with the one or more processors, during the first portion of the sleep session, the one or more sensory stimulators to deliver the sensory stimulation based on the output signals generated during the first portion of the sleep session; and determining, with the one or more processors, the demographic group for the user based on the sensory stimulation that is delivered during the first portion of the sleep session.

7. The method of claim 5, further comprising using the output signals generated during the first portion of the sleep session to determine the demographic group for the user based on a lack of an explicit demographic group designation for the user.

8. The method of claim 5, wherein the one or more sensory stimulators comprise a tone generator, and wherein the target variable comprises a number of tones that would be delivered during simulated sleep sessions.

9. A system for delivering sensory stimulation to a user during a sleep session, the system comprising:

means for generating output signals conveying information related to brain activity of the user during the sleep session;

means for providing the sensory stimulation to the user during the sleep session;

means for determining a demographic group for the user based on the output signals generated during a first portion of the sleep session;

means for selecting, during the sleep session, a stimulation parameter model associated with the demographic group of the user from a set of stimulation parameter models associated with different demographic groups;

means for controlling, during a second portion of the sleep session, the means for providing the sensory stimulation to deliver the sensory stimulation to the user based on the stimulation parameter model for the demographic group of the user and the output signals generated during the second portion of the sleep session, the second portion of the sleep session being subsequent in time to the first portion of the sleep session;

means for obtaining historical brain activity information for a population of users in a given demographic group, the historical brain activity information indicating sleep depth over time during sleep sessions of the population of users;

means for performing simulations of sensory stimulation based on (i) the historical brain activity information and (ii) one or more stimulation control parameters;

means for adjusting, at multiple times during each of the simulations, the one or more stimulation control parameters such that the simulation is performed based on the one or more stimulation control parameters as adjusted at the multiple times;

means for determining, with respect to each of the adjustments, an effect of the adjustment of the one or more stimulation control parameters on a target variable;

means for determining, based on the effects of the adjustments, a set of stimulation control parameters for a given stimulation parameter model associated with the given demographic group; and means for storing the given stimulation parameter model as part of the set of stimulation parameter models.

10. The system of claim 9, further comprising:

means for controlling, during the first portion of the sleep session, the means for providing sensory stimulation to deliver the sensory stimulation based on the output signals generated during the first portion of the sleep session; and means for determining the demographic group for the user based on the sensory stimulation that is delivered during the first portion of the sleep session.

11. The system of claim 9, wherein the output signals generated during the first portion of the sleep session are used to determine the demographic group for the user based on a lack of an explicit demographic group designation for the user.

12. The system of claim 9, wherein the means for providing sensory stimulation comprise a tone generator, and wherein the target variable comprises a number of tones that would be delivered during simulated sleep sessions.

* * * * *